United States Patent
Naidu

(10) Patent No.: US 11,426,557 B2
(45) Date of Patent: Aug. 30, 2022

(54) STABILIZATION DEVICE, SYSTEM, AND METHODS THEREOF FOR INTEGRATED CATHETERS

(71) Applicant: Becton, Dickinson and Company, Franklin Lakes, NJ (US)

(72) Inventor: Jithendra Kumar Sathyanarayana Naidu, Woodlands (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 136 days.

(21) Appl. No.: 16/825,834

(22) Filed: Mar. 20, 2020

(65) Prior Publication Data

US 2020/0297975 A1    Sep. 24, 2020

Related U.S. Application Data

(60) Provisional application No. 62/822,721, filed on Mar. 22, 2019.

(51) Int. Cl.
*A61M 25/02* (2006.01)

(52) U.S. Cl.
CPC ....... *A61M 25/02* (2013.01); *A61M 2025/024* (2013.01); *A61M 2025/0266* (2013.01)

(58) Field of Classification Search
CPC .... A61M 2025/024; A61M 2025/0266; A61M 25/02; A61M 2025/0246; A61M 2025/0253; A61M 2025/028
See application file for complete search history.

(56) References Cited

U.S. PATENT DOCUMENTS

| 2002/0068904 A1* | 6/2002 | Bierman | A61M 25/02 604/180 |
| 2006/0270994 A1* | 11/2006 | Bierman | A61M 25/02 604/180 |
| 2009/0143741 A1 | 6/2009 | Burn | |
| 2009/0182283 A1 | 7/2009 | Sloan | |
| 2013/0345639 A1 | 12/2013 | Spittler | |

OTHER PUBLICATIONS

PCT/US2020/024010 filed Mar. 20, 2020 International Search Report and Written Opinion dated Jun. 2, 2020.

* cited by examiner

*Primary Examiner* — Deanna K Hall
(74) *Attorney, Agent, or Firm* — Rutan & Tucker LLP

(57) ABSTRACT

A stabilization device for integrated catheters can include a platform, a pair of catheter fasteners on the platform, and a pair of stabilization wings extending from the platform. The platform can include a skin-facing side and catheter-securing side of the platform. The pair of catheter fasteners can be on the catheter-securing side of the platform. The catheter fasteners can be configured to secure a hub of an integrated catheter having an extension port. The pair of stabilization wings can extend from a transverse axis of the platform. The stabilization wings can be configured to mitigate rotation of the integrated catheter about a longitudinal axis thereof when the integrated catheter is secured by the catheter fasteners on the platform and the stabilization device is adhered to a patient. A method for stabilizing integrated catheters can include securing an integrated catheter and adhering the stabilization device to a patient's skin.

20 Claims, 8 Drawing Sheets

STABILIZATION DEVICE, SYSTEM, AND METHODS THEREOF FOR INTEGRATED CATHETERS

PRIORITY

This application claims the benefit of priority to U.S. Provisional Application No. 62/822,721, filed Mar. 22, 2019, which is incorporated by reference in its entirety into this application.

BACKGROUND

A peripheral intravenous catheter ("PIVC") often needs to be prematurely removed from a patient before an intended IV therapy is complete. A primary factor contributing to the need to prematurely remove a PIVC is mechanical phlebitis, which results when the PIVC moves and irritates the internal anatomy of the patient. A secondary factor contributing to the need to prematurely remove a PIVC is potential introduction of microorganisms when the PIVC moves while within the patient. Mechanical stabilization of PIVCs has been shown to decrease mechanical phlebitis and increase IV-therapy dwell time. However, existing stabilization devices for such PIVCs are not compatible with integrated PIVCs. Thus, the existing stabilization devices cannot provide the mechanical stabilization needed to reduce mechanical phlebitis and enhance the dwell time needed to complete intended IV therapies with integrated PIVCs. Disclosed herein is a stabilization device and methods thereof for integrated catheters such as integrated PIVCs.

SUMMARY

Disclosed herein is a stabilization device for integrated catheters including, in some embodiments, a platform, a pair of catheter fasteners on the platform, and a pair of stabilization wings extending from the platform. The platform has a skin-facing side and catheter-securing side of the platform. The pair of catheter fasteners is on the catheter-securing side of the platform. The catheter fasteners are configured to secure a hub of an integrated catheter having an extension port. The pair of stabilization wings extend from a transverse axis of the platform. The stabilization wings are configured to mitigate rotation of the integrated catheter about a longitudinal axis thereof when the integrated catheter is secured by the catheter fasteners on the platform and the stabilization device is adhered to a patient.

In some embodiments, the platform is configured with a degree of flexibility enabling the platform to conform to a contour of the patient at a stabilization site thereof.

In some embodiments, the skin-facing side of the platform has an adhesive thereon configured to adhere to skin of the patient.

In some embodiments, the stabilization device further includes a pad of a foam-like material having a skin-facing side and a platform-facing side of the pad. The pad is configured with a degree of compressibility enabling the pad to conform to a contour of the patient at a stabilization site thereof.

In some embodiments, the skin-facing side of the pad has an adhesive thereon configured to adhere to skin of the patient.

In some embodiments, the catheter fasteners are spaced apart from each other to accommodate the extension port of the integrated catheter between the catheter fasteners when the integrated catheter is secured by the catheter fasteners on the platform.

In some embodiments, at least one catheter fastener of the pair of catheter fasteners is a 'C'-shaped clip connected to the catheter-securing side of the platform.

In some embodiments, at least one catheter fastener of the pair of catheter fasteners is a clamp having a first jaw connected to the catheter-securing side of the platform and a second jaw connected to the first jaw by a living hinge.

In some embodiments, the platform includes a plurality of through holes configured to enable moisture between the stabilization device and the patient to escape through the through holes when the stabilization device is adhered to the patient.

In some embodiments, the transverse axis of the platform is an axis of symmetry of the platform.

Also disclosed herein is a stabilization device for integrated catheters including, in some embodiments, a platform, a pair of catheter fasteners on the platform, and a pair of stabilization wings extending from the platform. The platform is a polymer-based platform having a skin-facing side and catheter-securing side of the platform. The pair of catheter fasteners is on the catheter-securing side of the platform. The catheter fasteners are configured to secure a hub of an integrated catheter having an extension port. The pair of stabilization wings extend from a transverse axis of the platform. The stabilization wings are configured to mitigate rotation of the integrated catheter about a longitudinal axis thereof when the integrated catheter is secured by the catheter fasteners on the platform and the stabilization device is adhered to a patient. The platform having twofold symmetry about the transverse axis of the platform.

In some embodiments, the platform is configured with a degree of flexibility enabling the platform to conform to a contour of the patient at a stabilization site thereof. The skin-facing side of the platform has an adhesive thereon configured to adhere to skin of the patient.

In some embodiments, the stabilization device further includes a pad of a foam-like material having a skin-facing side and a platform-facing side of the pad. The pad is configured with a degree of compressibility enabling the pad to conform to a contour of the patient at a stabilization site thereof. The skin-facing side of the pad has an adhesive thereon configured to adhere to skin of the patient.

In some embodiments, the catheter fasteners are spaced apart from each other to accommodate the extension port of the integrated catheter between the catheter fasteners when the integrated catheter is secured by the catheter fasteners on the platform.

In some embodiments, at least one catheter fastener of the pair of catheter fasteners is a 'C'-shaped clip connected to the catheter-securing side of the platform. The 'C'-shaped clip is configured with a degree of flexibility enabling an opening of the 'C'-shaped clip to initially expand when the hub of the integrated catheter is inserted into the opening and subsequently contract when the hub of the integrated catheter is inserted past the opening.

In some embodiments, at least one catheter fastener of the pair of catheter fasteners is a clamp having a first jaw connected to the catheter-securing side of the platform and a second jaw connected to the first jaw by a living hinge. The clamp is configured with a snap between the first jaw and the second jaw configured to snap the first and second jaws together after the hub of the integrated catheter is inserted into the clamp.

In some embodiments, the platform includes a plurality of through holes configured to enable moisture between the stabilization device and the patient to escape through the through holes when the stabilization device is adhered to the patient.

Also disclosed herein is a method for stabilizing integrated catheters including, in some embodiments, securing a hub of an integrated catheter in a pair of catheter fasteners on a catheter-securing side of a platform of a stabilization device, the catheter fasteners spaced apart from each other to accommodate an extension port of the integrated catheter between the catheter fasteners; removing an adhesive backing from a skin-facing side of the stabilization device to expose an adhesive; and adhering the stabilization device to skin at a stabilization site near a percutaneous insertion site of a patient, thereby stabilizing the integrated catheter and decreasing risk of mechanical phlebitis.

In some embodiments, securing the hub of the integrated catheter in the pair of catheter fasteners includes expanding an opening of at least one 'C'-shaped clip of the pair of catheter fasteners upon inserting the hub into the 'C'-shaped clip and allowing the opening of the 'C'-shaped clip to contract upon inserting the hub past the opening of the of the 'C'-shaped clip.

In some embodiments, securing the hub of the integrated catheter in the pair of catheter fasteners includes enclosing the hub within at least one clamp of the pair of catheter fasteners and snapping the clamp closed around the hub. The clamp has a first jaw connected to the catheter-securing side of the platform and a second jaw connected to the first jaw by a living hinge.

In some embodiments, the methods further includes degreasing the patient's skin at the stabilization site with a degreasing wipe before adhering the platform to the skin of the patient.

These and other features of the concepts provided herein will become more apparent to those of skill in the art in view of the accompanying drawings and following description, which disclose particular embodiments of such concepts in greater detail.

DRAWINGS

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

With respect to terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

Figure 1:
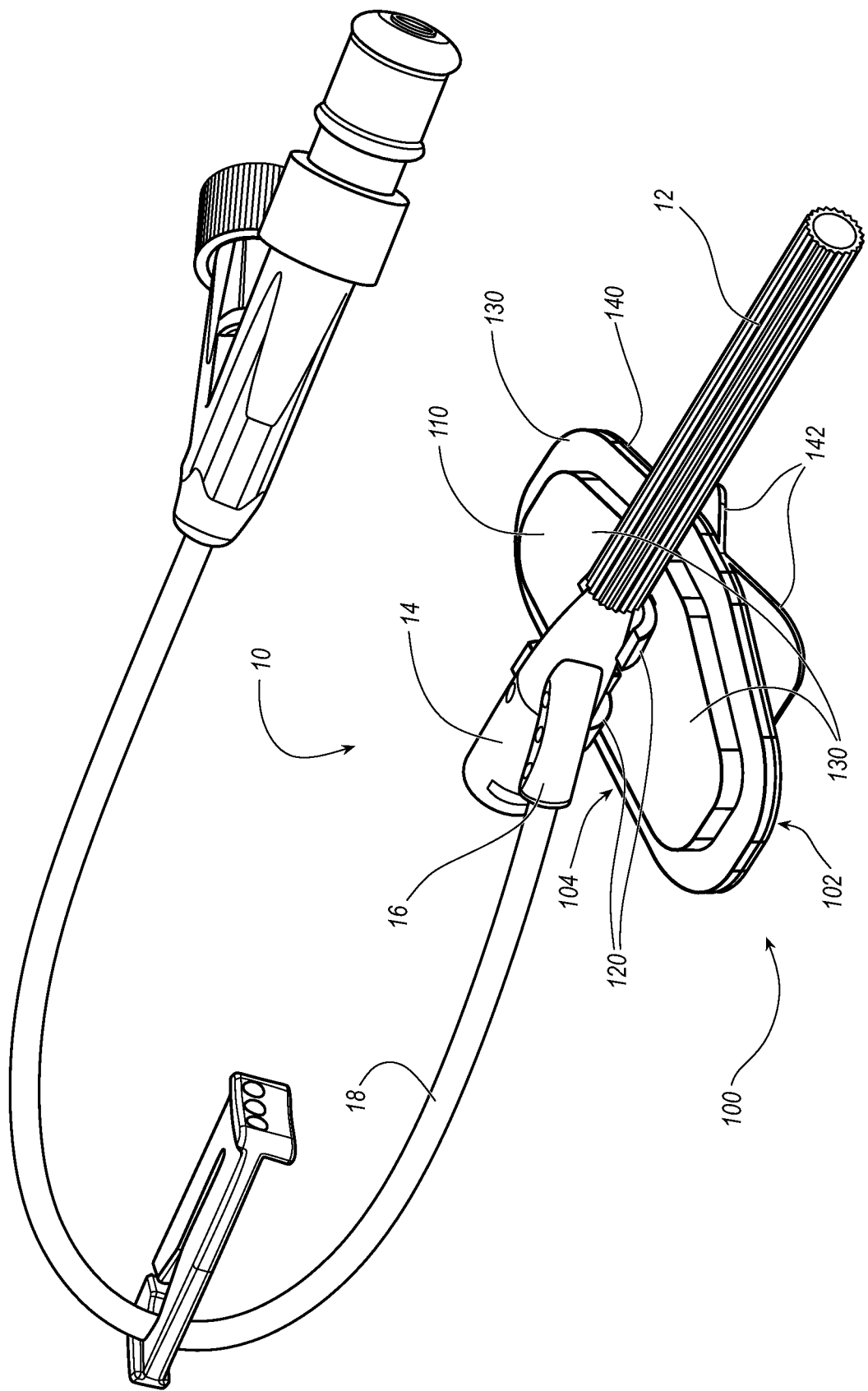
FIG. 1 illustrates a stabilization device for integrated catheters including an integrated catheter in accordance with some embodiments.

With respect to "integrated catheter," an integrated catheter is a one-piece manufacturer-assembled device including a catheter tube fluidly connected to at least one extension tube by way of a hub therebetween. Such an integrated catheter is shown in FIG. 1 by way of integrated catheter 10, which includes a catheter tube 12, a hub 14, an extension port 16 extending from the hub 14, and an extension tube 18 connected to the extension port 16. An integrated catheter is different than a non-integrated catheter, which must be assembled by a clinician or the like prior to use.

With respect to "proximal," as in a "proximal portion" or a "proximal end portion" of, for example, a catheter disclosed herein, "proximal" refers to a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," as in a "distal portion" or a "distal end portion" of, for example, a catheter disclosed herein, "distal" refers to a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

Again, a PIVC often needs to be prematurely removed from a patient before an intended IV therapy is complete. A primary factor contributing to the need to prematurely remove a PIVC is mechanical phlebitis, which results when the PIVC moves and irritates the internal anatomy of the patient. A secondary factor contributing to the need to prematurely remove a PIVC is potential introduction of microorganisms when the PIVC moves while within the patient. Mechanical stabilization of PIVCs has been shown to decrease mechanical phlebitis and increase IV-therapy dwell time. However, existing stabilization devices for such PIVCs are not compatible with integrated PIVCs. Thus, the existing stabilization devices cannot provide the mechanical stabilization needed to reduce mechanical phlebitis and enhance the dwell time needed to complete intended IV therapies with integrated PIVCs. Disclosed herein is a stabilization device and methods thereof for integrated catheters such as integrated PIVCs.

For example, a stabilization device for integrated catheters is disclosed including, in some embodiments, a platform, a pair of catheter fasteners on the platform, and a pair of stabilization wings extending from the platform. The platform has a skin-facing side and catheter-securing side of the platform. The pair of catheter fasteners is on the catheter-securing side of the platform. The catheter fasteners are configured to secure a hub of an integrated catheter having an extension port. The pair of stabilization wings extend from a transverse axis of the platform. The stabilization wings are configured to mitigate rotation of the integrated catheter about a longitudinal axis thereof when the integrated catheter is secured by the catheter fasteners on the platform and the stabilization device is adhered to a patient. Also, a method for stabilizing integrated catheters with the stabilization device is disclosed.

Stabilization Device

FIG. 1 illustrates a stabilization device 100 for integrated catheters such as the integrated catheter 10 in accordance with some embodiments.

As shown in FIG. 1, some embodiments of the stabilization device 100 include a platform 110, a pair of catheter fasteners 120 on the platform 110, and a pair of stabilization wings 130 extending from the platform 110. The stabilization device 100, or the platform 110 thereof, has a skin-facing side 102 and catheter-securing side 104. The pair of catheter fasteners 120 is on the catheter-securing side 104 of the platform 110. The catheter fasteners 120 are configured to secure the hub 14 of the integrated catheter 10 with (or without) the extension port 16. As shown and described in more detail below with reference to FIGS. 4-6, the pair of stabilization wings 130 extend from a transverse axis 412 of the platform 110. The stabilization wings 130, which are shown as sweeping back from a distal end portion to a proximal end portion of the stabilization device 100, are configured to mitigate rotation of the integrated catheter 10 about a longitudinal axis thereof when both the integrated catheter 10 is secured by the catheter fasteners 120 on the platform 110 and the stabilization device 100 is adhered to a patient.

Also shown in FIG. 1, some embodiments of the stabilization device 100 also include a pad 130 adhered to the platform 110 and an adhesive backing 140 with optional wings 142 configured to facilitate removal of the adhesive backing from the pad 130 (or the platform 110, or the like, in some embodiments) for adhering the stabilization device 100 to a patient at a stabilization site thereof.

For expository expediency, "the stabilization device 100" of FIG. 1 is sometimes used herein to generically refer to some or all of the disclosed stabilization devices. In such instances, a certain component (e.g., "the platform 110") of the stabilization device 100 is sometimes used herein to generically refer to some or all of the disclosed stabilization-device components of the same kind. Because the stabilization device 100 and the components thereof can have unique features (e.g., the height $h_1$ of the platform 110 is greater than the height $h_2$ of the platform 510), context determines how "the stabilization device 100" and the components thereof are used.

Figure 2:
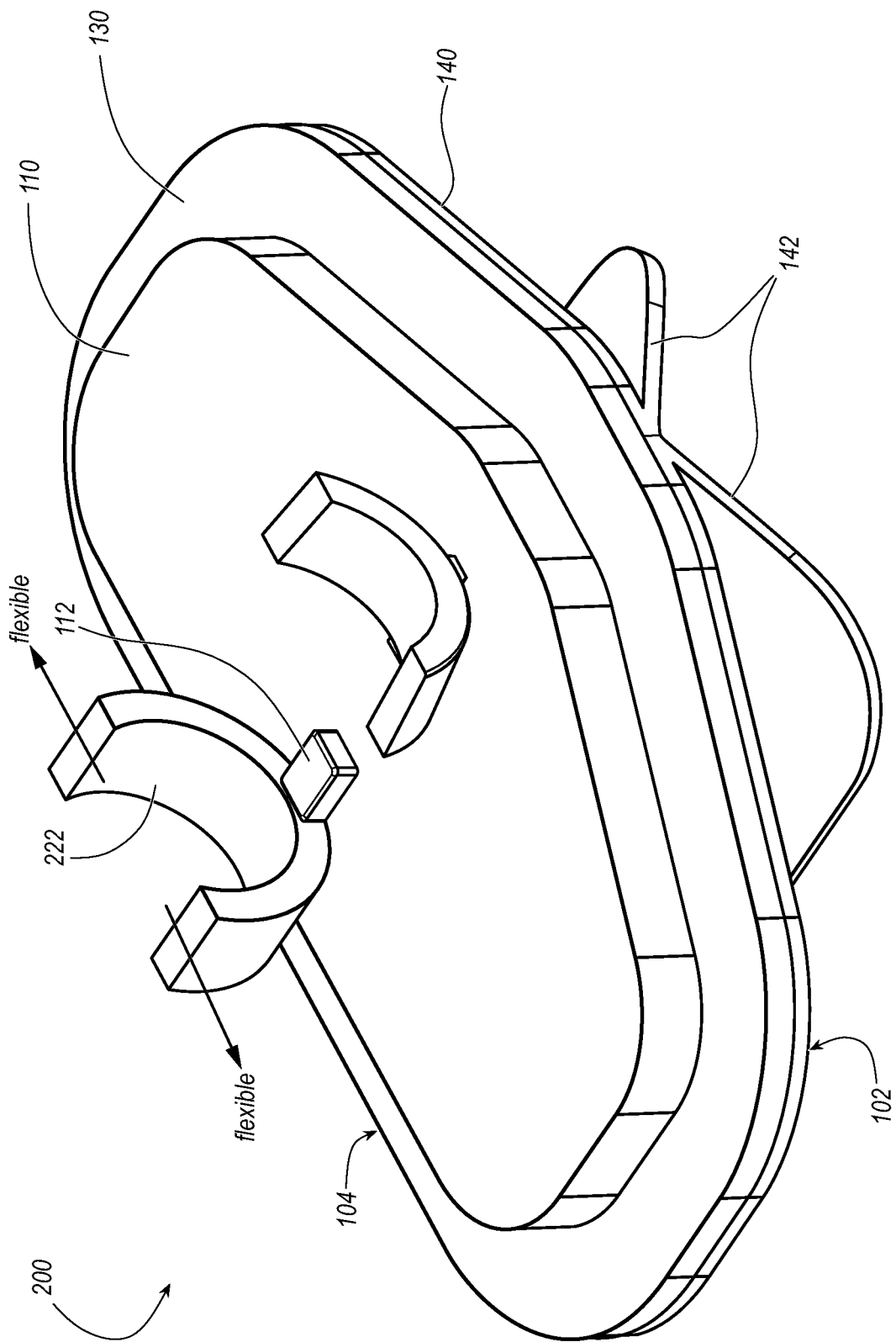
FIG. 2 illustrates a stabilization device including a 'C'-shaped clip for a catheter fastener in accordance with some embodiments.
Figure 3:
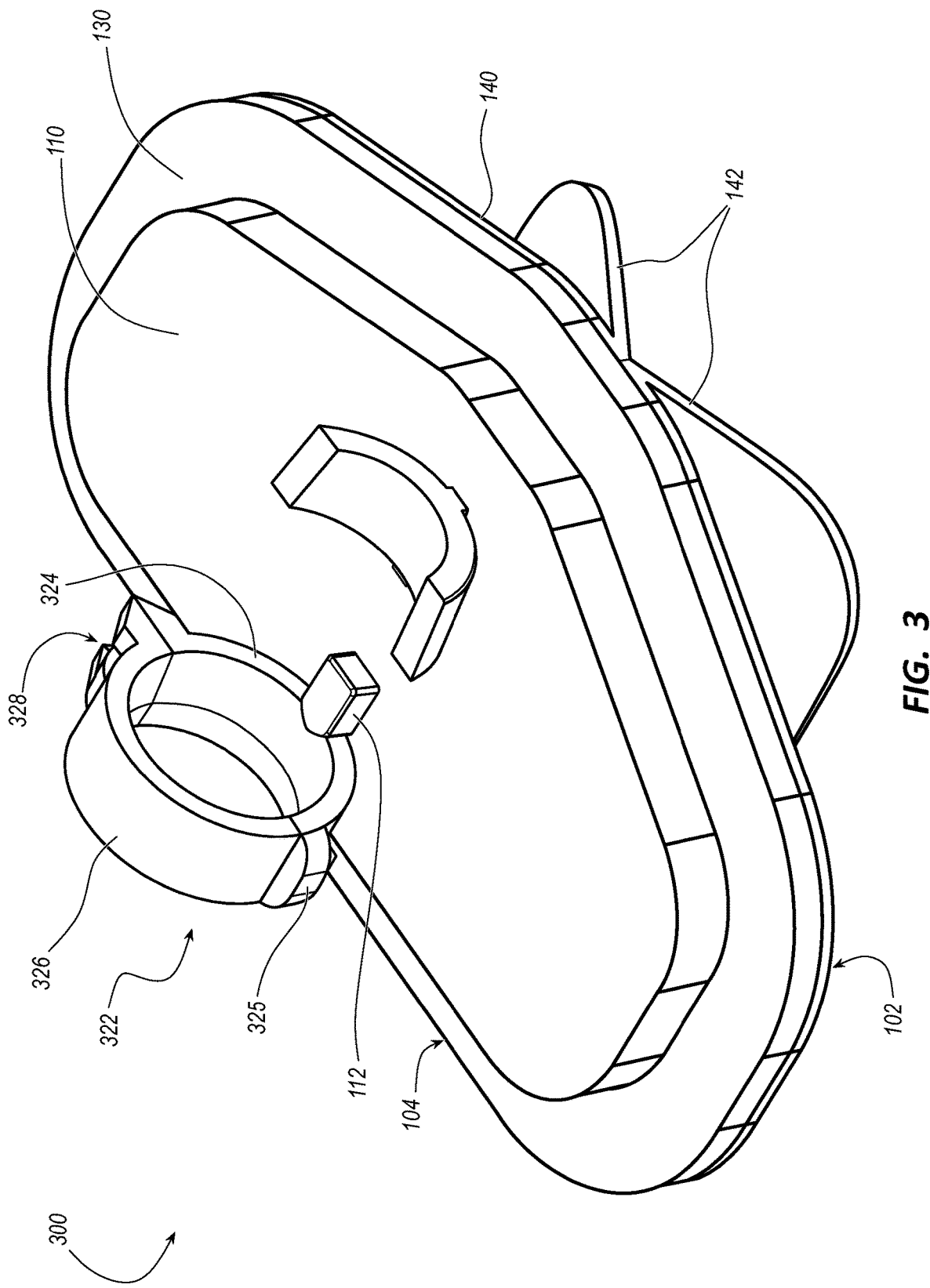
FIG. 3 illustrates a stabilization device including a clamp for a catheter fastener in accordance with some embodiments.

FIG. 2 illustrates a stabilization device 200 including at least one 'C'-shaped clip 222 for a catheter fastener of the catheter fasteners 120 in accordance with some embodiments. FIG. 3 illustrates a stabilization device 300 including at least one clamp 322 for a catheter fastener of the catheter fasteners 120 in accordance with some embodiments.

As shown in FIGS. 2 and 3, the catheter fasteners 120 in some embodiments of the stabilization device 100 such as the stabilization devices 200 and 300 are spaced apart from each other to accommodate the extension port 16 of the integrated catheter 10 between the catheter fasteners 120 when the integrated catheter 10 is secured by the catheter fasteners 120 on the platform 110. Between the catheter fasteners 120, the stabilization device 100 optionally includes a hub support 112 configured to support the hub 14 of the integrated catheter 10 between the catheter fasteners 120 when the integrated catheter 10 is secured by the catheter fasteners 120 on the platform 110.

As shown in FIG. 2, at least one catheter fastener of the pair of catheter fasteners 120 of the stabilization device 200 is the 'C'-shaped clip 222 connected to the catheter-securing side 104 of the platform 110. The 'C'-shaped clip 222 is configured with a degree of flexibility enabling an opening of the 'C'-shaped clip to initially expand when the hub 14 of the integrated catheter 10 is inserted into the opening. The 'C'-shaped clip 222 is configured to subsequently contract when the hub 14 of the integrated catheter 10 is inserted past the opening and seated in the 'C'-shaped clip 222.

As shown in FIG. 3, at least one catheter fastener of the pair of catheter fasteners 120 of the stabilization device 300 is the clamp 322 having a first jaw 324 connected to the catheter-securing side 104 of the platform 110 and a second jaw 326 connected to the first jaw 324 by a living hinge 325. The clamp 322 is configured with a snap 328 between the first jaw 324 and the second jaw 326 configured to snap the first jaw 324 and the second jaw 326 together when the hub 14 of the integrated catheter 10 is seated into the clamp 322.

Figure 4:
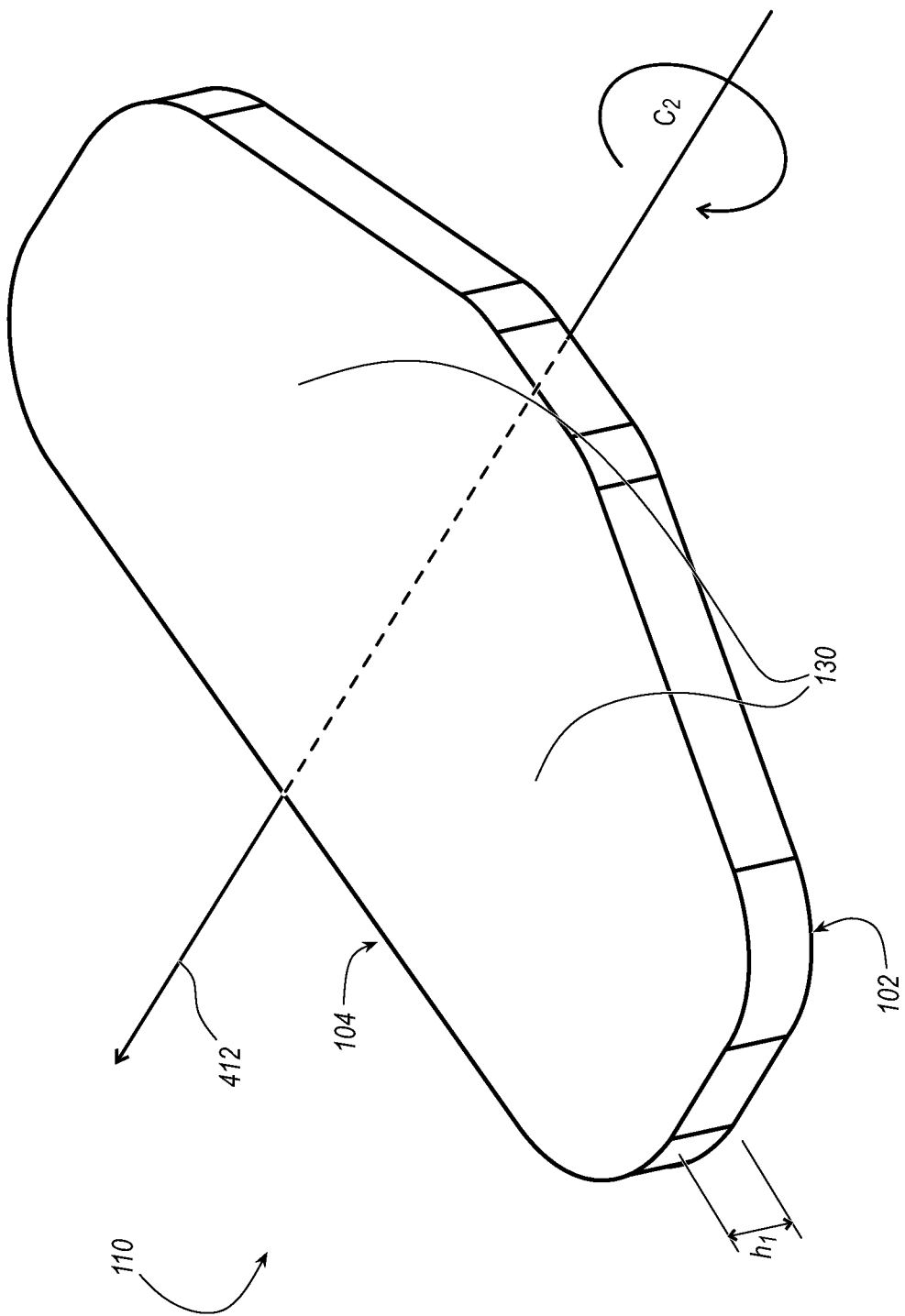
FIG. 4 illustrates a first platform for a stabilization device in accordance with some embodiments.
Figure 5:
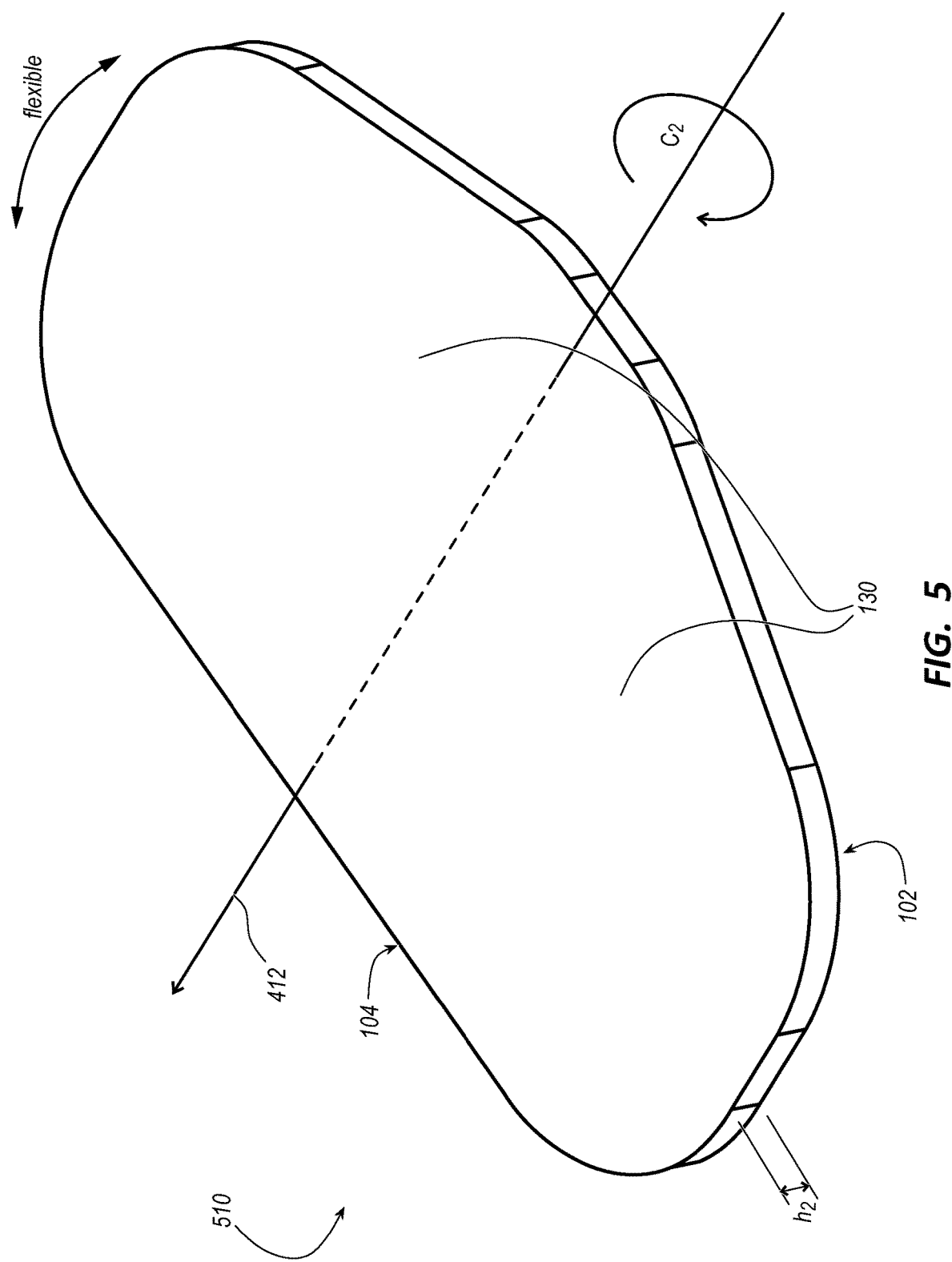
FIG. 5 illustrates a second platform for a stabilization device in accordance with some embodiments.
Figure 6:
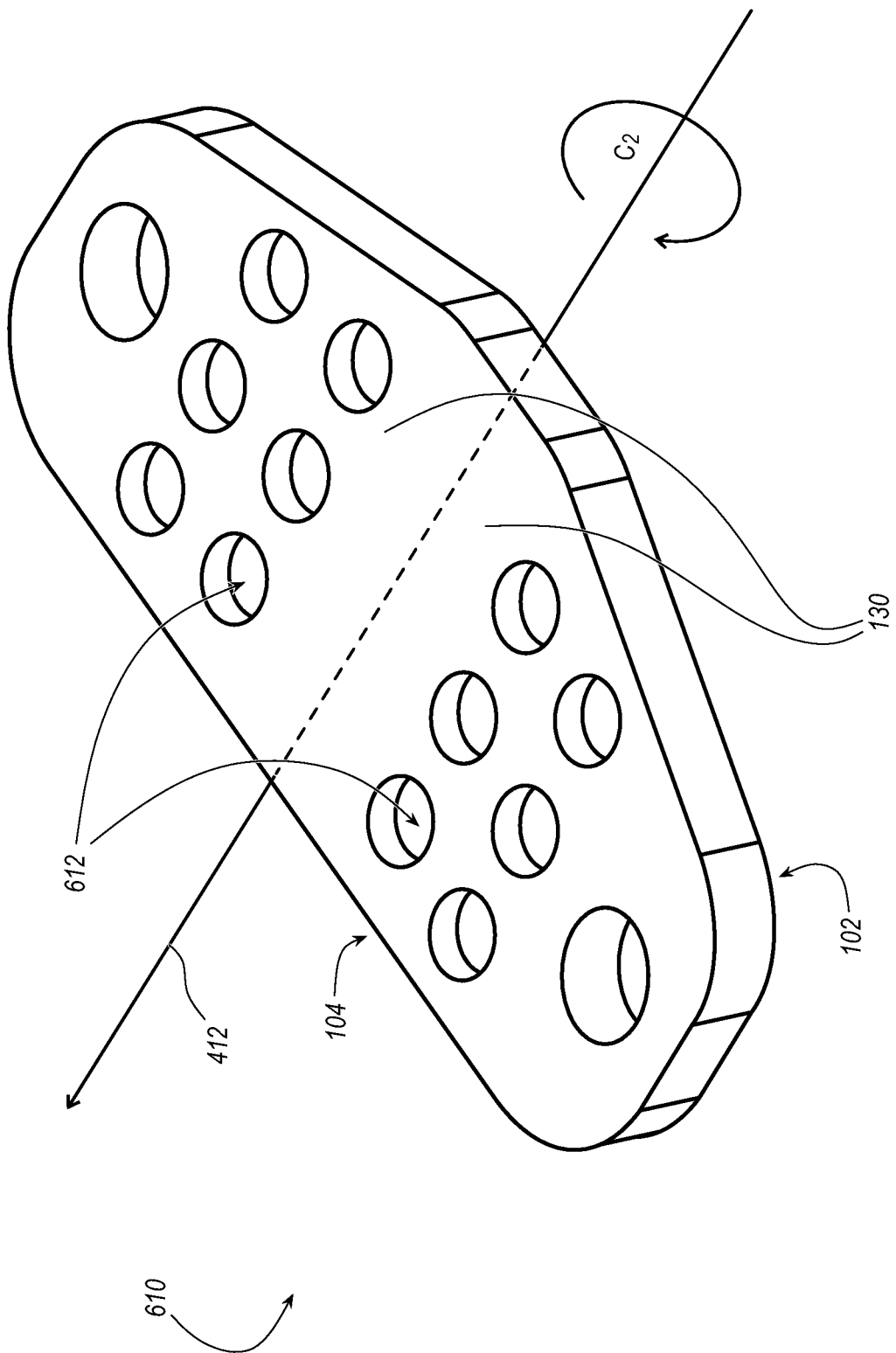
FIG. 6 illustrates a third platform for a stabilization device in accordance with some embodiments.
Figure 7:
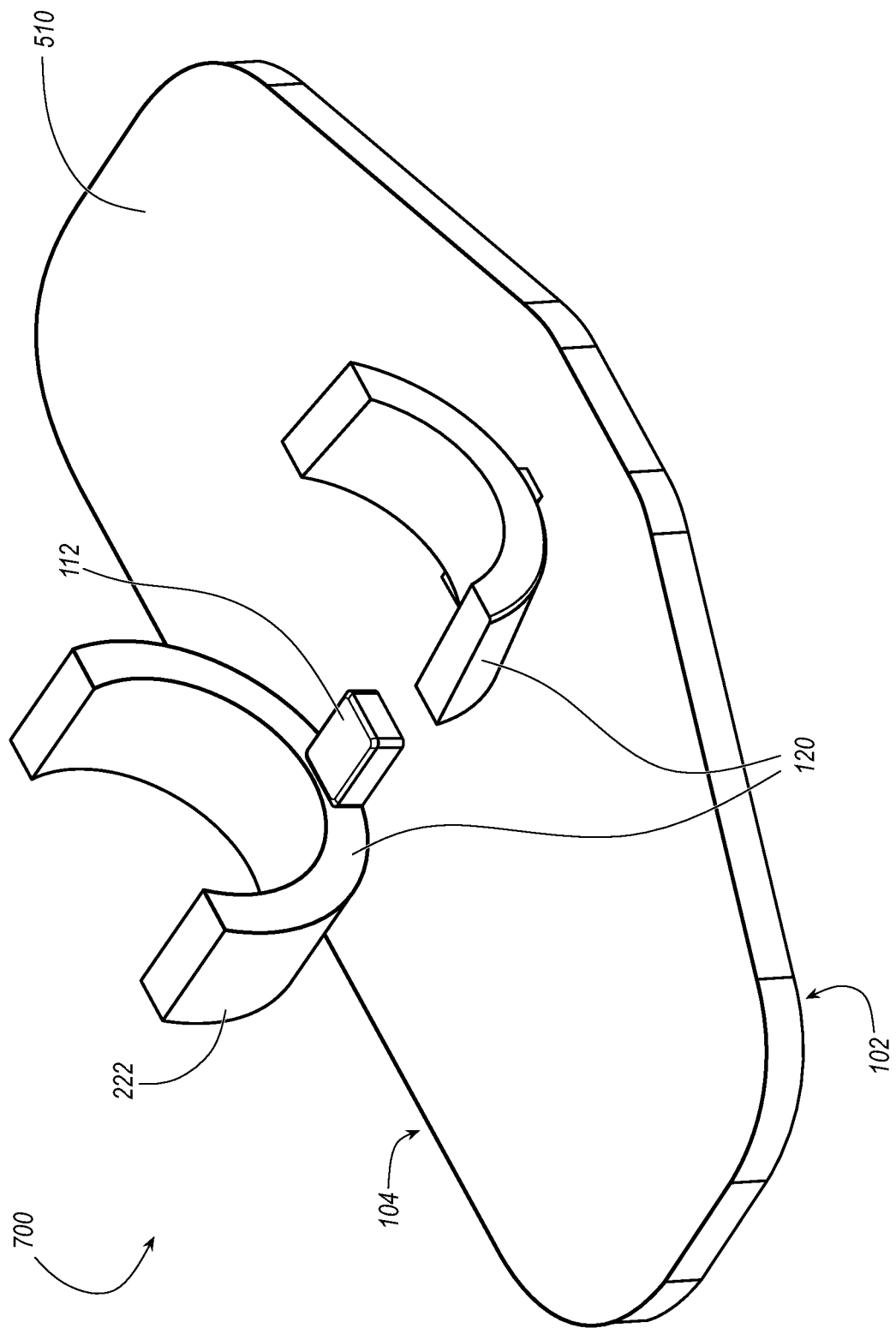
FIG. 7 illustrates a stabilization device including the platform of FIG. 5 in accordance with some embodiments.
Figure 8:
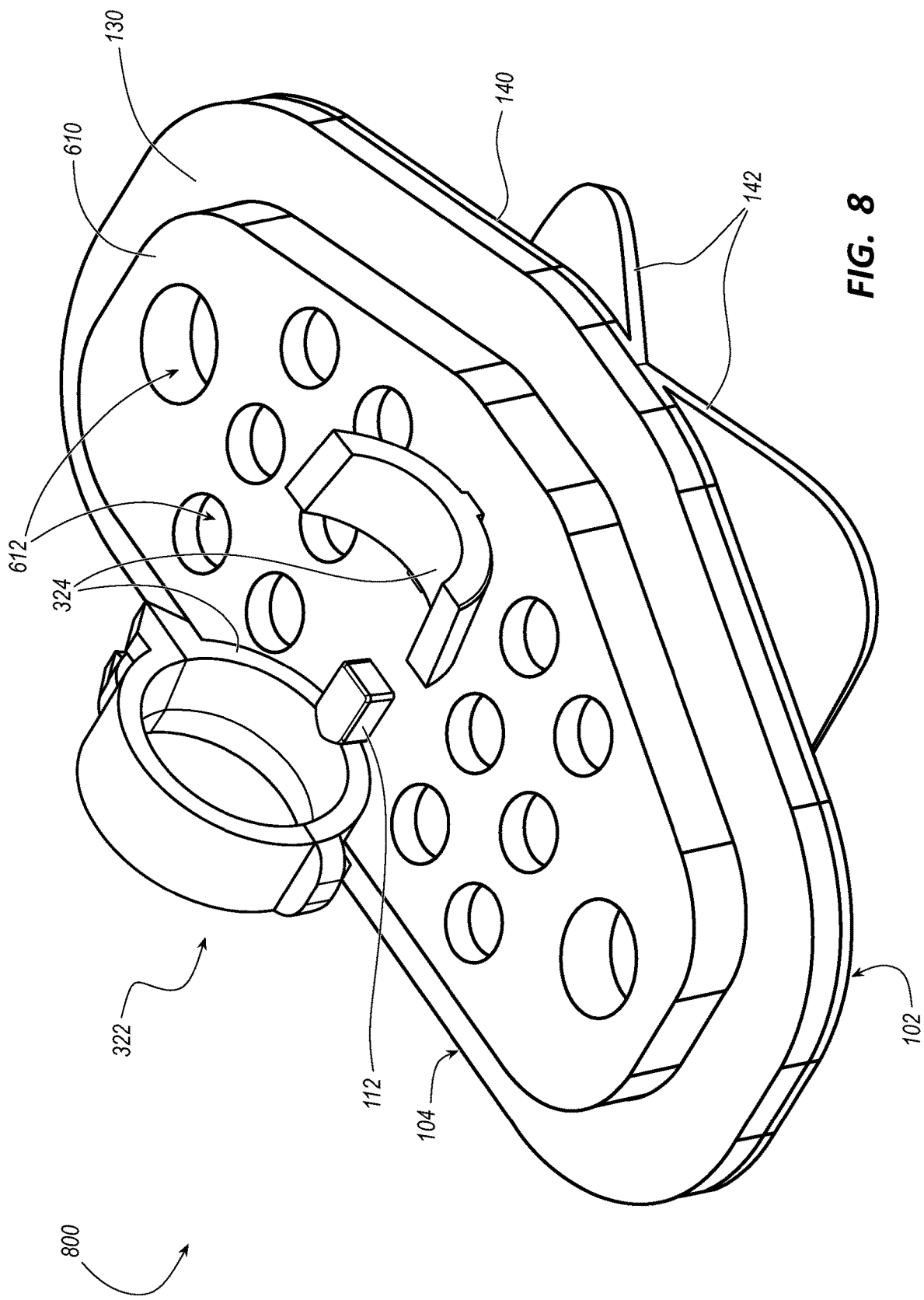
FIG. 8 illustrates a stabilization device including the platform of FIG. 6 in accordance with some embodiments.

FIG. 4 illustrates a first platform (i.e., the platform 110) for the stabilization device 100 in accordance with some embodiments. FIG. 5 illustrates a second platform 510 for the stabilization device 100 in accordance with some embodiments. FIG. 6 illustrates a third platform 610 for the stabilization device 100 in accordance with some embodiments. FIG. 7 illustrates a stabilization device 700 including the platform 510 of FIG. 5 in accordance with some embodiments. FIG. 8 illustrates a stabilization device 800 including the platform 610 of FIG. 6 in accordance with some embodiments.

As shown in FIGS. 4, 5, and 6, each platform of the platforms 110, 510, and 610 includes the transverse axis 412 from which the pair of stabilization wings 130 extend. The transverse axis 412 is an axis of symmetry about which the platform 110, 510, or 610 has twofold rotational symmetry (i.e., $C_2$ symmetry).

As shown in FIG. 5, the platform 510 has a height $h_2$ that is less than a height $h_1$ of the platform 110. Being as the platform 510 is relatively thin and formed of a medically acceptable polymer as described below, the platform 510 is configured with a degree of flexibility enabling the platform 510 to conform to a contour (e.g., a body contour) of a patient at a stabilization site thereof near a percutaneous insertion site for the integrated catheter 10. In contrast, while the platform 110 can be formed of the same polymer as the platform 510, the platform 110 has little to no appreciable flexibility due to the height $h_1$ of the platform 110 being greater than the height $h_2$ of the platform 510. For this reason, the platform 110 is often used with the pad 130, which has a degree of compressibility as described herein. In some embodiments, the platform 510 is also used with the pad 130, thereby increasing conformation of the stabilization device 100 to the contour (e.g., the body contour) of the patient.

The skin-facing side 104 of the platform 510 includes an adhesive (e.g., pressure-sensitive adhesive) thereon configured to adhere to the skin of the patient as with the stabilization device 700 of FIG. 7, from which the adhesive backing 140 is removed for clarity. Alternatively, like the platform 110, the skin-facing side 104 of the platform 510 is adhered to the pad 130, which pad 130, in turn, includes an adhesive (e.g., pressure-sensitive adhesive) on the skin-facing side 104 of the pad 130 configured to adhere to the skin of the patient upon removal of the adhesive backing 140. The adhesive between the pad 130 and the platform 510 that adheres the pad 130 and the platform 510 together can be the same or different then than the adhesive that adheres the stabilization device to the patient.

With respect to the pad 130, the pad 130 of the stabilization device 100 is formed of a medically acceptable foam-like material having a degree of compressibility also enabling the pad 130 to conform to a contour (e.g., a body contour) of a patient at a stabilization site thereof near a percutaneous insertion site for the integrated catheter 10. Again, the skin-facing side 104 of the pad 130 includes an adhesive (e.g., pressure-sensitive adhesive) thereon configured to adhere to the skin of the patient. (See, for example, the stabilization device 200 of FIG. 2, the stabilization device 300 of FIG. 3, or the stabilization device 800 of FIG. 8.)

As shown in FIG. 6, the platform 610 includes a plurality of through holes 612, or breathing holes, configured to enable moisture between, for example, the stabilization device 800 of FIG. 8 and the skin of the patient to escape through the through holes 612 when the stabilization device 800 is adhered to the patient. While not shown, the platform 510 can also include the plurality of through holes 612.

The platform 110, 510, or 610 is formed of a polymeric material such as by injection molding. For example, the platform 510, which is relatively thin and flexible compared to the platform 110, can be formed by injection molding including thin-wall molding. The pair of catheter fasteners 120 can be molded together with the platform 110, 510, or 610 or coupled to the platform 110, 510, or 610 after each of the pair of fasteners 120 and the platform 110, 510, or 610 is molded.

In view of the foregoing description, it should be understood any platform 110, 510, or 610, or a combination thereof, disposed on the pad 130 or not, can include any pair of catheter fasteners 120 described herein to form a stabilization device such as the stabilization device 200, 300, 700, or 800.

Kit

The stabilization device 100, instructions for use of the stabilization device 100, and any one or more additional components selected from the integrated catheter 10, an antimicrobial pad (e.g., BIOPATCH®, GuardIVa®), a topical medicament optionally including an antimicrobial agent, a skin adhesive optionally including an antimicrobial agent, and a degreasing wipe can be packaged as a ready-to-use stabilization kit.

Method

A method for stabilizing integrated catheters such as the integrated catheter 10 includes, in some embodiments, securing the hub 14 of the integrated catheter 10 in the pair of catheter fasteners 120 on the catheter-securing side 104 of the platform 110 of the stabilization device 100, the catheter fasteners 120 spaced apart from each other to accommodate the extension port 16 of the integrated catheter 10 between the catheter fasteners 120; removing an adhesive backing 140 from the skin-facing side 102 of the stabilization device 100 to expose the adhesive; and adhering the stabilization device 100 to skin of the patient at a stabilization site thereof near a percutaneous insertion site, thereby stabilizing the integrated catheter 10 and decreasing risk of mechanical phlebitis.

Securing the hub 14 of the integrated catheter 10 in the pair of catheter fasteners 120 includes expanding the opening of the 'C'-shaped clip 222 of the pair of catheter fasteners 120 upon inserting the hub 14 into the 'C'-shaped clip 222 and allowing the opening of the 'C'-shaped clip 222 to contract upon inserting the hub 14 past the opening of the of the 'C'-shaped clip 222. Alternatively, securing the hub 14 of the integrated catheter 10 in the pair of catheter fasteners 120 includes enclosing the hub 14 within the clamp 322 of the pair of catheter fasteners 120 and snapping the clamp 322 closed around the hub 14.

The method can further include accessing the percutaneous insertion site in one or more ways of accessing the insertion site such as passing the catheter tube 12 of the integrated catheter 10 into the insertion site.

The method can further include treating the percutaneous insertion site after accessing the insertion site. Treating the insertion site can include placing the antimicrobial pad (e.g., BIOPATCH®, GuardIVa®) around the insertion site to keep the insertion site free of infection. Treating the insertion site can include applying the topical medicament optionally including the antimicrobial agent around the insertion site or sealing the insertion site with the skin adhesive optionally including a same or different antimicrobial agent. Not only does sealing the insertion site with the skin adhesive prevent microbes from entering the insertion site, but sealing the insertion site has the added effect of further stabilizing the integrated catheter 10 to the patient, thereby further decreasing mechanical phlebitis.

The method can further include degreasing the skin of the patient at the stabilization site with a degreasing wipe before adhering the stabilization device 100 to the skin of the patient.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A stabilization device for integrated catheters, comprising:
a platform having a skin-facing side and catheter-securing side of the platform;
a pair of catheter fasteners positioned on the catheter-securing side of the platform, the pair of catheter fasteners including a first catheter fastener separated and disconnected from a second catheter fastener, the pair of catheter fasteners configured to secure a hub of an integrated catheter having an extension port; and
a pair of stabilization wings positioned under the platform and extending from a transverse axis of the platform, the pair of stabilization wings configured to mitigate rotation of the integrated catheter about a longitudinal axis thereof when the integrated catheter is secured by the pair of catheter fasteners on the platform and the stabilization device is adhered to a patient.

2. The stabilization device of claim 1, wherein the platform is configured with a degree of flexibility enabling the platform to conform to a contour of the patient at a stabilization site thereof.

3. The stabilization device of claim 1, wherein the skin-facing side of the platform has an adhesive thereon configured to adhere to skin of the patient.

4. The stabilization device of claim 1, further comprising a pad of a foam-like material having a skin-facing side and a platform-facing side of the pad, the pad configured with a degree of compressibility enabling the pad to conform to a contour of the patient at a stabilization site thereof.

5. The stabilization device of claim 4, wherein the skin-facing side of the pad has an adhesive thereon configured to adhere to skin of the patient.

6. The stabilization device of claim 1, wherein the separation between the first catheter fastener and the second catheter fastener is configured to accommodate the extension port of the integrated catheter between the pair of catheter fasteners when the integrated catheter is secured by the pair of catheter fasteners on the platform.

7. The stabilization device of claim 1, wherein the first catheter fastener of the pair of catheter fasteners is a 'C'-shaped clip connected to the catheter-securing side of the platform.

8. The stabilization device of claim 1, wherein the first catheter fastener of the pair of catheter fasteners is a clamp having a first jaw connected to the catheter-securing side of the platform and a second jaw connected to the first jaw by a living hinge.

9. The stabilization device of claim 1, wherein the platform includes a plurality of through holes configured to enable moisture between the stabilization device and the patient to escape through the through holes when the stabilization device is adhered to the patient.

10. The stabilization device of claim 1, wherein the transverse axis of the platform is an axis of symmetry of the platform.

11. A stabilization device for integrated catheters, comprising:
a polymer-based platform having a skin-facing side and catheter-securing side of the platform;
a pair of catheter fasteners positioned on the catheter-securing side of the platform, the pair of catheter fasteners including a first catheter fastener separated and disconnected from a second catheter fastener, the pair of catheter fasteners configured to secure a hub of an integrated catheter having an extension port; and
a pair of stabilization wings positioned under the platform and extending from a transverse axis of the platform, the pair of stabilization wings configured to mitigate rotation of the integrated catheter about a longitudinal axis thereof when the integrated catheter is secured by the pair of catheter fasteners on the platform and the stabilization device is adhered to a patient, the platform having twofold symmetry about the transverse axis of the platform.

12. The stabilization device of claim 11, wherein:
the platform is configured with a degree of flexibility enabling the platform to conform to a contour of the patient at a stabilization site thereof, and
the skin-facing side of the platform has an adhesive thereon configured to adhere to skin of the patient.

13. The stabilization device of claim 11, further comprising a pad of a foam-like material having a skin-facing side and a platform-facing side of the pad, the pad configured with a degree of compressibility enabling the pad to conform to a contour of the patient at a stabilization site thereof, wherein the skin-facing side of the pad has an adhesive thereon configured to adhere to skin of the patient.

14. The stabilization device of claim 11, wherein the separation between the first catheter fastener and the second catheter fastener is configured to accommodate the extension port of the integrated catheter between the pair of catheter fasteners when the integrated catheter is secured by the pair of catheter fasteners on the platform.

15. The stabilization device of claim 11, wherein the first catheter fastener is a 'C'-shaped clip connected to the catheter-securing side of the platform, and wherein the 'C'-shaped clip is configured with a degree of flexibility enabling an opening of the 'C'-shaped clip to initially expand when the hub of the integrated catheter is inserted into the opening and subsequently contract when the hub of the integrated catheter is inserted past the opening.

16. The stabilization device of claim 11, wherein: the first catheter fastener of the pair of catheter fasteners is a clamp having a first jaw connected to the catheter-securing side of the platform and a second jaw connected to the first jaw by a living hinge, and wherein the clamp is configured with a snap between the first jaw and the second jaw configured to snap the first and second jaws together after the hub of the integrated catheter is inserted into the clamp.

17. The stabilization device of claim 11, wherein the platform includes a plurality of through holes configured to enable moisture between the stabilization device and the patient to escape through the through holes when the stabilization device is adhered to the patient.

18. A method for stabilizing integrated catheters, comprising:
securing a hub of an integrated catheter in a pair of catheter fasteners positioned on a catheter-securing side of a platform of a stabilization device, the pair of catheter fasteners spaced apart and disconnected from each other to accommodate an extension port of the integrated catheter between the pair of catheter fasteners;
removing an adhesive backing from a skin-facing side of the stabilization device to expose an adhesive; and adhering the stabilization device to skin at a stabilization site near a percutaneous insertion site of a patient, thereby stabilizing the integrated catheter and decreasing risk of mechanical phlebitis.

19. The method of claim 18, wherein the step of securing the hub of the integrated catheter in the pair of catheter fasteners includes expanding an opening of at least one 'C'-shaped clip of the pair of catheter fasteners upon inserting the hub into the 'C'-shaped clip and allowing the opening of the 'C'-shaped clip to contract upon inserting the hub past the opening of the of the 'C'-shaped clip.

20. The method of claim 18, wherein the step of securing the hub of the integrated catheter in the pair of catheter fasteners includes enclosing the hub within at least one clamp of the pair of catheter fasteners and snapping the clamp closed around the hub, the clamp having a first jaw connected to the catheter-securing side of the platform and a second jaw connected to the first jaw by a living hinge.

\* \* \* \* \*